(12) United States Patent
Giuliani et al.

(10) Patent No.: US 9,944,591 B2
(45) Date of Patent: Apr. 17, 2018

(54) ACTIVE COMPOUND AND RELATED COMPOSITION FOR DERMATOLOGICAL USE IN THE PHARMACEUTICAL OR COSMETIC FIELD

(71) Applicant: GIULIANI S.P.A., Milan (IT)

(72) Inventors: Giammaria Giuliani, Milan (IT); Anna Benedusi, Milan (IT); Barbara Marzani, Carbonara Al Ticino (IT); Sergio Baroni, Villa d'Adda (IT); Elena Pini, Milan (IT)

(73) Assignee: Giuliani S.p.A., Milan (IT)

( * ) Notice: Subject to any disclaimer, the term of this patent is extended or adjusted under 35 U.S.C. 154(b) by 0 days.

(21) Appl. No.: 15/501,997

(22) PCT Filed: Aug. 4, 2015

(86) PCT No.: PCT/EP2015/067882
§ 371 (c)(1),
(2) Date: Feb. 6, 2017

(87) PCT Pub. No.: WO2016/020350
PCT Pub. Date: Feb. 11, 2016

(65) Prior Publication Data
US 2017/0240502 A1 Aug. 24, 2017

(30) Foreign Application Priority Data
Aug. 5, 2014 (IT) .............................. MI2014A1435

(51) Int. Cl.
*C07C 233/49* (2006.01)
*A61K 8/44* (2006.01)
(Continued)

(52) U.S. Cl.
CPC .............. *C07C 233/49* (2013.01); *A61K 8/44* (2013.01); *A61K 31/197* (2013.01); *A61K 31/42* (2013.01);
(Continued)

(58) Field of Classification Search
CPC ................................ A61K 31/197; A61K 8/42
See application file for complete search history.

(56) References Cited

FOREIGN PATENT DOCUMENTS

EP 2407163 A1 1/2012

OTHER PUBLICATIONS

Essr et al., "Contact Sensitizers Induce Skin Inflammation via ROS Production and Hyaluronic Acid Degradation," PLOS One 7(7):e41340 (2012).
(Continued)

*Primary Examiner* — San Ming R Hui
(74) *Attorney, Agent, or Firm* — LeClairRyan PLLC (57) ABSTRACT

The invention relates to the 4-((2E,4E,6E)-octa-2,6,4-trienamid)butanoic acid; its use in the therapeutic and cosmetic field for topical application to the skin to achieve a combined antioxidant activity against ROS together with an anti-inflammatory effect and an effect of promoting the production of hyaluronic acid, so as to oppose at the same time the oxidizing action of free radicals and inflammatory effects, in order to preserve the physiological conditions of human epidermis and skin homeostasis and prevent skin aging (anti-aging); the compositions for therapeutic and cosmetic use which comprise 4-((2E,4E,6E)-octa-2,6,4-trienamid)butanoic acid as active ingredient, formulated with excipients for topical use suitable for local administration on the skin.

10 Claims, 8 Drawing Sheets

(51) Int. Cl.
*A61Q 19/00* (2006.01)
*A61K 31/197* (2006.01)
*A61K 31/42* (2006.01)

(52) U.S. Cl.
CPC ........ *A61Q 19/007* (2013.01); *A61K 2800/74* (2013.01)

(56) References Cited

OTHER PUBLICATIONS

Flori et al., "2,4,6-Octatrienoic Acid is a Novel Promoter of Melanogenesis and Antioxidant Defence in Normal Human Melanocytes via PPAR-gamma activation," Pigment Cell & Melanoma Research 24:618-630 (2011).
International Search Report and Written Opinion corresponding to PCT/EP2015/067882, filed Aug. 4, 2015 (dated Nov. 5, 2015).

ACTIVE COMPOUND AND RELATED COMPOSITION FOR DERMATOLOGICAL USE IN THE PHARMACEUTICAL OR COSMETIC FIELD

This application is a national stage application under 35 U.S.C. § 371 of PCT Application No. PCT/EP2015/067882, filed Aug. 4, 2015, which claims priority of Italy Application No. MI2014A001435, filed Aug. 5, 2014, which are hereby incorporated by reference in their entirety.

FIELD OF THE INVENTION

The present invention relates to a new active compound and to a composition for pharmaceutical or cosmetic dermatological use.

BACKGROUND ART

The skin, the largest organ of the human body, is the first barrier against physical, chemical and biological stress, thus providing the first protection against harmful environmental agents while preventing dehydration.

The skin barrier is a very complex system consisting of a large number of closely interrelated components. Changing any of these components results in an alteration of the barrier function culminating in skin alterations and diseases.

Recent studies have shown that the damage to the skin barrier is at the center of the onset of diseases, being still in discussion whether it is a primary cause or a secondary effect: opposing hypothesis see, on the one hand, skin alterations as triggers of the inflammation, on the other hand, damage to the barrier as an effect of the inflammatory response to allergens or irritants.

The alteration of the barrier and of immunological mechanisms can play an important role in promoting and supporting skin lesions and inflammation. Skin inflammation is associated with an abnormal acute or chronic condition. The skin inflammatory response involves a series of complex interactions between cellular mediators, i.e. keratinocytes, mast cells and macrophages, and molecular mediators such as cytokines and chemokines.

It is known that an uncontrolled release of reactive oxygen species (ROS) is involved in aging and in various skin pathologies. In fact, there are many agents able to produce an oxidative stress condition to the skin, including UV, pollutant, contaminant, additive and food preservative exposure, as well as side effects of some drugs.

The presence of free radicals and moisture loss are the main causes of skin alterations, in particular of skin aging.

Hyaluronic acid is a primary component of glycosaminoglycans, intercellular key substances responsible for skin hydration. Because of its physical and chemical properties, in fact, it is able to absorb and retain large amounts of water. Over time, the content of hyaluronic acid in the skin tends to decrease with a progressive decrease in the level of hydration, turgescence and tissue plasticity.

In addition to its moisturizing function, hyaluronic acid is a molecule essential for the formation of the collagen matrix and elastic fibers and plays an important role in preventing cell and tissue damage from physical stress. Recently, its involvement in the contact sensitization process, such as in ACD, allergic contact dermatitis, has also been highlighted.

Skin inflammation mediated by the innate immune system is a crucial step in the sensitization to contact allergens. The study of Philipp R. Esser et al., Contact Sensitizers Induce Skin Inflammation via ROS Production and Hyaluronic Acid Degradation, PLoS ONE, www.plosone.org Jul. 1, 2012, Volume 7, Issue 7, e41340, shows that the application of sensitizing agents leads to a degradation of hyaluronic acid, whose fragments trigger the inflammatory process. ROS are involved in this process because the degradation of hyaluronic acid is ROS-dependent.

The object of the present invention is to provide an efficient means of prevention and treatment of alterations and disorders of the skin, such as sensitization, aging, oxidative stress, inflammation, skin diseases in general and, in particular, of inflammatory origin, a means having also an action of skin barrier recovery and in particular of reactivation of the natural hydration capacity of the connective tissues. According to such an object, it is desired to at least safeguard, if not improve, the integrity and functionality of the skin barrier and homeostasis.

SUMMARY OF THE INVENTION

Such objects and other advantages that can be inferred hereafter in the present description are achieved using a new active ingredient, and corresponding composition for pharmaceutical or cosmetic use containing it, consisting of 4-((2E,4E,6E)-octa-2,4,6-trienamid)butanoic acid of formula:

or pharmaceutically acceptable salts or derivatives thereof.

DESCRIPTION OF THE INVENTION

As demonstrated by experimental studies described hereafter in the present description, such a compound has a strong antioxidant, anti-inflammatory and moisturizing activity which allow an effective dermatological use with a plurality of combined effects, suitable for the prevention and treatment of skin diseases, especially those that involve sensitization and inflammation conditions, a use suitable for retaining the skin homeostasis and also for the cosmetic treatment of skin aging (anti-aging).

The objects of the present invention therefore are:
- the compound 4-((2E, 4E, 6E)-octa-2,4,6-trienamid)butanoic acid
- its use in the therapeutic and cosmetic field for topical application to the skin to achieve a combined antioxidant activity against ROS together with an anti-inflammatory effect and an effect of promoting production of hyaluronic acid, so as to oppose at the same time the oxidizing action of free radicals and inflammatory conditions, in order to preserve the physiological conditions of human epidermis and skin homeostasis.
- compositions for therapeutic and cosmetic use that include 4-((2E,4E,6E)-octa-2,4,6-trienamid)butanoic acid as active ingredient, or salts or other pharmaceutically acceptable derivatives thereof, formulated with excipients for topical use suitable for local administration on the skin, in particular for the following indications:
- dermatological use in the prevention and treatment of skin diseases.

dermatological use in the prevention and treatment of skin sensitization conditions.

use in the treatment of allergic contact dermatitis.

dermatological use in the prevention and treatment of skin inflammation conditions.

dermatological use in skin treatment for retaining skin homeostasis.

dermatological use in skin treatment to promote the production of hyaluronic acid, and hence the properties of resistance and retention of properties such as hydration, turgidity, plasticity and viscosity typical of hyaluronic acid.

cosmetic use against skin aging (anti-aging action).

According to the invention, a composition is preferred comprising 4-((2E, 4E, 6E)-octa-2,4,6-trienamid)butanoic acid, or salts thereof or other pharmaceutically acceptable derivatives, as active ingredient, in an amount in the range from 0.4 mM to 56 mM.

Preferred ranges of amounts of active ingredient in the composition expressed as parts by weight, w/w %, for example include the following: 0.01-0.05; 0.125-0.375; 0.25-0.75; 0.5-1; 0.75-1.25.

EXAMPLES

The following are non limiting examples of synthesis of the compound of the invention and of a composition suitable, in particular, for the uses specified above.

Synthesis of 4-((2E, 4E, 6E)-octa-2,4,6-trienamid)butanoic acid: $C_{12}H_{17}NO_3$. PM: 223

Place 164 mg (1.59 mmoles) of γ-aminobutyric acid (GABA) under magnetic stirring in 5 ml of anhydrous THF keeping in ice bath; when the temperature reaches 0° C., drip 3 ml of a solution of NaOH 1N and then a solution consisting of 1,447 mmoles of octatrienoic acid chloride (obtained starting from 200 mg, 1,447 mmol acid) in 3 ml anhydrous THF. After such an addition, the mixture is returned to room temperature and kept under nitrogen stream and magnetic stirring away from light for 12 h. Add 5 ml of HCl 2N to the solution and extract with 10 ml AcOEt; wash the organic phase with brine. Dry the organic phase on $Na_2SO_4$, filter and evaporate. Control on TLC: hexane/ethyl acetate 7:3. Purification on chromatographic column eluting with hexane/ethyl acetate 7:3.

Characterization spectra of the compound of the invention are shown in the figures of the accompanying drawings as described hereafter.

In the following non-limiting examples of composition, the conventional INCI nomenclature is used and the amounts of components are expressed in percentages by weight on the weight of the composition, variable within the relative designated ranges.

Example 1

FACIAL CREAM

| Component (INCI name) | w/w % |
| --- | --- |
| Cyclopentasiloxane | 20-40 |
| C30-45 Alkyl cetearyl dimethicone crosspolymer | 1-3 |
| Polysilicone-11 | 2-3 |

-continued

FACIAL CREAM

| Component (INCI name) | w/w % |
| --- | --- |
| Dimethicone | 1.25-2.25 |
| Butylene glycol | 2-4 |
| HDI/trimethylol hexyllactone crosspolymer | 2-4 |
| Steareth-2 | 1-2 |
| Ammonium acryloyldimethyltaurate/VP copolymer | 0.5-1.5 |
| Stearic acid | 0.5-1.5 |
| Glycerin | 0.5-1.5 |
| Inositol | 0.5-1.5 |
| Steareth-21 | 0.5-1.5 |
| Phenoxyethanol | 0.7-1.1 |
| Polymethyl methacrylate | 0.7-1.1 |
| Dicaprylyl carbonate | 0.6-0.9 |
| Caprylyl glycol | 0.5-0.7 |
| *Borago officinalis* seed oil | 0.25-0.75 |
| Parfum | 0.1-0.4 |
| Diazolidinyl Urea | 0.1-0.3 |
| *Persea gratissima* oil | 0.02-0.06 |
| 4-((2E,4E,6E)-octa-2,4,6-trienamid)butanoic acid | 0.01-0.05 |
| Betaine | 0.05-0.15 |
| Sorbityl furfural | 0.05-0.15 |
| Panthenol | 0.05-0.15 |
| Xanthan gum | 0.05-0.15 |
| Tetrasodium glutamate diacetate | 0.02-0.06 |
| Pentaerythrityl tetra-di-t-butyl hydroxyhydrocinnamate | 0.025-0.075 |
| Sodium hyaluronate | 0.025-0.075 |
| Tocotrienols | 0.01-0.03 |
| Dimethylmethoxy chromanol | 0.005-0.015 |
| Rutin | 0.005-0.015 |
| Aqua | q.s. ad 100 |

Example 2

SILICONE SERUM

| Component (INCI name) | w/w % |
| --- | --- |
| Cyclopentasiloxane | 20-30 |
| Dimethiconol | 5-15 |
| 1,3-Butylene glycol | 2-4 |
| Vitamin E acetate | 0.05-0.2 |
| 4-((2E,4E,6E)-octa-2,4,6-trienamid)butanoic acid | 0.25-0.75 |
| Parfum | 0.01-0.03 |
| Dimethicone crosspolymer | q.s. ad 100 |

Example 3

BODY CREAM

| Component (INCI name) | w/w % |
| --- | --- |
| Glycerin | 4-6 |
| Sorbitan stearate | 2.5-4.5 |
| Sucrose cocoate | 0.2-0.6 |
| C10-18 Triglycerides | 3-5 |
| Ethylhexyl palmitate | 3-5 |
| Squalane | 2-4 |
| Cyclopentasiloxane | 1-3 |
| *Calendula officinalis* flower extract | 0.5-1.5 |
| Sodium hydroxymethylglycinate | 0.2-0.6 |
| Tapioca starch | 0.3-0.7 |
| *Oryza sativa* wax | 0.25-0.75 |
| Phenoxyethanol | 0.25-0.75 |
| Lactic acid 80% sol | 0.2-0.6 |
| Allantoin | 0.2-0.4 |
| Betaine | 0.2-0.4 |
| Xanthan gum | 0.2-0.4 |

BODY CREAM

| Component (INCI name) | w/w % |
| --- | --- |
| Inositol | 0.2-0.4 |
| Xylitol | 0.2-0.4 |
| Parfum | 0.15-0.35 |
| Glycyrrhetinic acid | 0.1-0.3 |
| Cetyl hydroxyethylcellulose | 0.1-0.3 |
| Beta sitosterol | 0.05-0.15 |
| 4-((2E,4E,6E)-octa-2,4,6-trienamid)butanoic acid | 0.125-0.375 |
| Disodium EDTA | 0.05-0.15 |
| Sorbityl furfural | 0.05-0.15 |
| Taurine | 0.05-0.15 |
| Aqua | q.s. ad 100 |

Example 4

LIGHT FACIAL CREAM

| Component (INCI name) | w/w % |
| --- | --- |
| Ethylhexyl methoxycinnamate | 2-6 |
| Dicaprylyl carbonate | 1-5 |
| Potassium azeloyl diglycinate | 0.25-0.75 |
| Octocrylene | 1-3 |
| Butyl methoxydibenzoylmethane | 0.5-2.5 |
| C12-15 Alkyl benzoate | 0.5-2.5 |
| 4-((2E,4E,6E)-octa-2,4,6-trienamid)butanoic acid | 0.5-1 |
| Phenoxyethanol | 0.5-1.5 |
| Ethylhexylglycerin | 0.05-0.15 |
| Algae extract | 0.025-0.075 |
| Carbomer | 0.25-0.75 |
| Sodium hydroxide | 0.4-0.8 |
| Cyclopentasiloxane | 0.25-0.75 |
| Dimethicone/vinyl dimethicone crosspolymer | 0.01-0.05 |
| Acrylamide/sodium acryloyldimethyltaurate copolymer | 0.1-0.3 |
| Isohexadecane | 0.1-0.3 |
| Polysorbate 80 | 0.02-0.06 |
| Parfum | 0.25-0.65 |
| Sodium benzoate | 0.2-0.4 |
| Acrylates/C10-30 alkyl acrylate crosspolymer | 0.1-0.3 |
| Disodium EDTA | 0.05-0.15 |
| Sorbityl furfural | 0.05-0.15 |
| Vitamin E acetate | 0.05-0.15 |
| Lecithin | 0.02-0.06 |
| Aqua | q.s. ad 100 |

Example 5

SUN CREAM

| Component (INCI name) | w/w % |
| --- | --- |
| Ethylhexyl methoxycinnamate | 8-12 |
| Diethylamino hydroxybenzoyl hexyl benzoate | 8-12 |
| C12-15 Alkyl benzoate | 6-10 |
| Dibutyl adipate | 5-9 |
| Ethylhexyl salicylate | 4-6 |
| Octocrylene | 4-6 |
| Titanium dioxide | 2-4 |
| Bis-ethylhexyloxyphenol methoxyphenyl triazine | 1-3 |
| Diethylhexyl butamido triazone | 1-3 |
| Silica | 1-2 |
| Bis-PEG/PPG-20/5 PEG/PPG-20/5 dimethicone | 1-2 |
| Methoxy PEG/PPG-25/4 dimethicone | 1-2 |
| Propylene glycol | 0.8-1 |
| Steareth-21 | 1-1.4 |
| Caprylic/capric triglyceride | 0.4-0.8 |
| Phenoxyethanol | 0.4-0.8 |

SUN CREAM

| Component (INCI name) | w/w % |
| --- | --- |
| Caprylyl glycol | 0.25-0.75 |
| Glycerin | 0.2-0.6 |
| Ammonium acryloyldimethyltaurate/VP copolymer | 0.2-0.4 |
| *Zea mays* oil | 0.1-0.3 |
| Lactic acid | 0.08-0.16 |
| Glycyrrhetinic acid | 0.05-0.15 |
| Sorbic acid | 0.05-0.09 |
| Disodium EDTA | 0.05-0.15 |
| 4-((2E,4E,6E)-octa-2,4,6-trienamid)butanoic acid | 0.75-1.25 |
| Sodium hydroxymethylglycinate | 0.3-0.7 |
| Tocopheryl acetate | 0.3-0.7 |
| Diethylhexyl syringylidenemalonate | 0.3-0.7 |
| Sorbityl furfural | 0.02-0.06 |
| Sodium hydroxide | 0.01-0.03 |
| *Calendula officinalis* flower extract | 0.01-0.03 |
| Ferulic acid | 0.005-0.015 |
| Aqua | q.s. ad 100 |

DRAWINGS

The diagrams according to FIGS. 1 to 4 in the accompanying drawings show the results for the experimental studies described hereafter.

FIGS. 5 to 8 relate to the following characterization spectra of the compound of the invention:

EXPERIMENTAL STUDIES

The activity of the compound of the invention was assessed using the following experimental studies.

Study of the Effects on the Production of ROS by DCFH-DA Assay

The production of ROS (reactive oxygen species) in the mouse fibroblast cell line BALB3T3 was determined by spectrofluorimetry with the 2,7-dichlorofluorescein-diacetate (DCFH-DA) assay, as described by Tobi and collaborators.

DCFH-DA is a non-fluorescent compound in its lipophilic form, able to diffuse through the cell membrane. Once inside the cell, it is deacetylated by the intracellular esterases to non-fluorescent 2,7-dichlorofluorescein (DCFH). Since DCFH is unable to re-cross the cell membrane, it accumulates in cells. The reaction with intracellular ROS leads to the oxidation of DCFH to 2,7-dichlorofluorescein (DCF), a highly fluorescent compound. The intensity of such a fluorescence can be detected with a fluorimeter, allowing the estimate of the amount of ROS produced in cells.

The immortalized line of human keratinocytes NCTC2544 is used (Perry V. P. et al., 1957), cultured in sterile flasks (25 cm$^3$), incubated at 37° C. in a humid atmosphere at 5% CO$_2$ in MEM (Minimum Essential Medium) added with 10% bovine fetal serum (FBS), 2 mm glutamine, 1% non-essential amino acids, in the presence of 1% penicillin and streptomycin.

The 1:3 split is done every 2 days upon achieving the monolayer by washing with 1×PBS (phosphate buffer without $Ca^{2+}$ and $Mg^{2+}$) and detachment of cells with a trypsin-EDTA solution at 37° C. for 2 minutes.

The protocol used for this experiment represents a modified version of the one described by Tobi and collaborators. Human keratinocytes NCTC2544 were seeded in 96-well plates at the density of $5*10^4$ cells/well and incubated until reaching about 80% confluence.

The cells were then pre-treated for 16 hours with a sample of the compound of the invention to the following different concentrations: 0.5 µM, 1 µM, 5 µM.

A sample of GABA, γ-aminobutyric acid, was used as comparison compound at a concentration 0.5 µM.

At the end of 16 hours, the cells were incubated for 30 min. with 0.1 mM solution of DCFH-DA (Sigma-Aldrich, St. Louis, Mo., USA).

At the end of incubation, cells were washed with PBS 1× and the oxidative stress was induced via 90-minute treatment with a solution of 1 mm $H_2O_2$, in the dark, at 37° C. and 5% $CO_2$.

After treatment, the cells were washed 2 times with PBS 1× and lysed with CelLytic™ lysis buffer (Sigma-Aldrich, St. Louis, Mo., USA) according to the manufacturer's protocol.

Then, the cells were transferred in a black 96-well plate and the fluorescence of DCF was read spectrofluorimetrically using a Fluoroskan Ascent FL Microplate Fluorescence Reader (Thermo Fisher Scientific Inc., Waltham, Mass., USA), with wavelengths of excitation and emission of 485 and 538 nm, respectively.

The emission values (RFU) obtained for each sample, related to the production of intracellular ROS, were compared to the emission value obtained for the negative control (Ctr=medium only), for the positive control (Ctr+$H_2O_2$=cells treated with $H_2O_2$ 1 mM) and expressed as a percentage of ROS produced according to the following equation:

$$\% \text{ ROS produced/Ctr} = (\text{Abs}_{538\,nm} \text{ sample}/\text{Abs}_{538\,nm} \text{ Ctr})*100$$

All the analyses were performed at least two times in duplicate.

Figure 1:
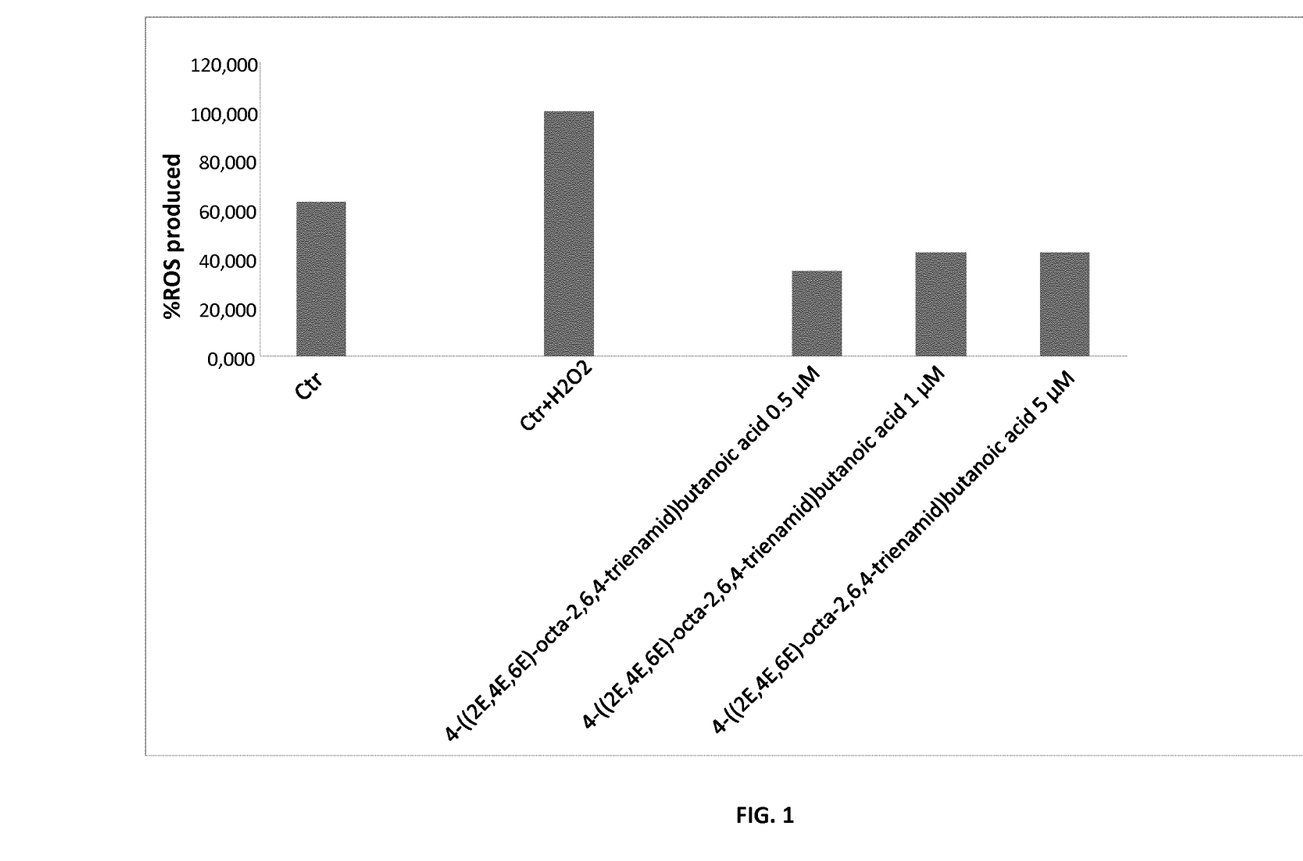
FIG. 1 and FIG. 2 show a chart for the production of ROS by DCFH-DA assay.
Figure 2:
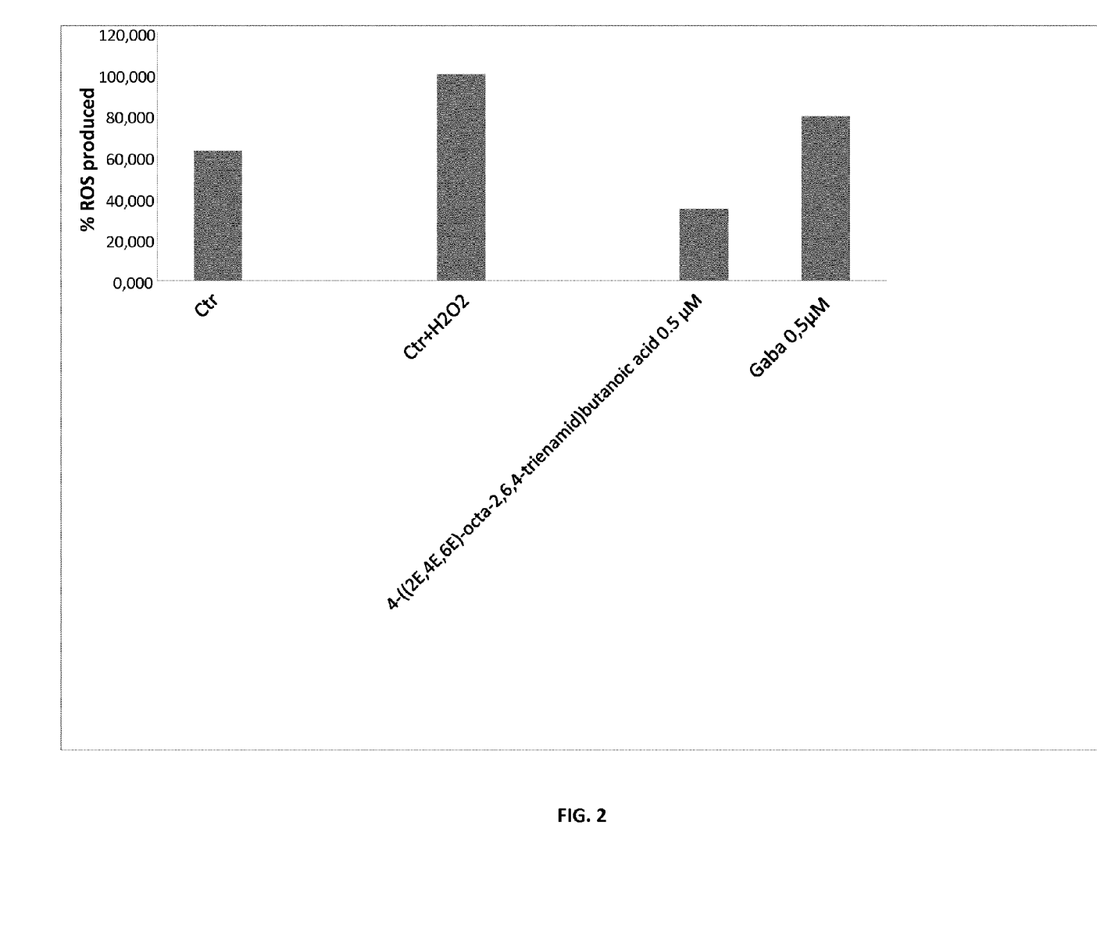

The results are summarized in the graphs in FIG. 1 and FIG. 2: FIG. 1 highlights the antioxidant activity of the compound of the invention in all the three different concentrations tested, while FIG. 2 highlights the superior antioxidant activity of the sample of compound of the invention compared to the above comparison compound GABA at the same concentration 0.5 µM.

Study of the Anti-Inflammatory Effects Through Gene Expression of TNF-Alpha on Keratinocytes In such further test, an immortalized line of human keratinocytes NCTC 2544 is used (Perry V. P. et al., 1957) cultured in sterile flasks (25 $cm^3$), incubated at 37° C. in a humid atmosphere at 5% $CO_2$ in culture medium MEM (Minimum Essential Medium) supplemented with 10% fetal bovine serum (FBS), 2 mM glutamine, 1% non-essential amino acids, in the presence of 1% penicillin and streptomycin.

Day 1: Cell Seeding

When the cells (human keratinocytes NCTC 2544) reached about 80% confluence, they were detached with trypsin/EDTA and seeded at a density of $1\times10^6$ cells/ml in 12-well plates and incubated at 37° C., 5% CO2 (24 h).

Day 2: Exposure to the Substances for 24 h

A sample of the compound of the invention is dissolved in DMSO (100%) at a concentration of 10 mM (stock solution), and then diluted in EMEM, supplemented with 2.5% FBS, 2 mM L-glutamine, 1% NEAA solution and 1% penicillin (10,000 U/ml)/streptomycin (10,000 pg/ml).

The controls, one containing only the culture medium (negative control=Control) and the other the culture medium+LPS (5 µg/ml) (positive control=Control+LPS) were included in each plate.

The cells were treated with the compound of the invention at a concentration equal to 5 µM. LPS at a concentration of 5 µg/ml was added to each well (except in the negative control).

Real-Time qPCR

The effect of the compounds object of the study on the gene expression of TNF-α was evaluated by quantitative RT-PCR (quantitative reverse transcription-polymerasechainreaction-qRT-PCR).

This analysis required 3 sequential steps:
extraction of total RNA;
retrotranscription in cDNA;
qRT-PCR.

Extraction of Total RNA from Human Keratinocytes NCTC 2544

Total RNA was extracted from cells NCTC 2544 using Tri Reagent (Sigma Aldrich) as described by Chomczynski and Mackey.

The use of Tri Reagent is an efficient method for extracting total RNA or for the simultaneous extraction of RNA, DNA and proteins from human samples. Isolated RNA may be used for several assays, including RT-PCR. The entire procedure can be completed in 1 hour and the recovery of non-degraded messenger RNA is 30-150% higher than other methods.

At the end of the incubation, the cells treated as above were washed with PBS (1×) and then lysed with Tri Reagent. Each lysate was transferred in an eppendorf and was further homogenized with an insulin syringe. Then, chloroform (200 µL) was added to the lysates and they were vortexed and let stand at room temperature for 15 minutes.

After centrifugation at 12000×g for 15 minutes at 4° C., 3 phases were obtained for each lysate: an organic phase containing proteins and cellular elements, a central phase containing the DNA (visible as a white ring) and an aqueous phase (colorless) containing the RNA. The aqueous phases were treated with isopropanol and the samples were left to rest overnight. The samples were centrifuged at 12000×g for 10 minutes at 4° C. The supernatant was removed and the pellets were washed with sterile ethanol at 75% and centrifuged again at 7500×g for 5 minutes at 4° C. The pellets were resuspended with 20 µL of DEPC water (treated with diethyl pyrocarbonate) and placed in a digital thermostatic bath (Swbd-STUART) at 56° C. for 15 minutes.

Using a spectrophotometer (Jenway UV/VIS MOD: 6715, BS-6715B0), concentrations were calculated in µg/mL of total RNA extracted at a wavelength of 260 nm.

Finally, the integrity of RNA (2 µg/mL) was assessed by means of an electrophoresis run on 1% agarose gel.

Retrotranscription in cDNA

Total RNA was converted into cDNA (complementary DNA), using an enzyme capable of synthesizing a DNA molecule using a strand of RNA as a template; this DNA-polymerase RNA-dependent enzyme is called reverse transcriptase.

It binds to the 3' end of a single strand of RNA and using random primers and deoxynucleoside triphosphate (DNTPS) synthezises the strand of cDNA.

To this end, a commercial kit "High-CapacitycDNA Reverse Transcription Kit (Applied Biosystems, Monza, Italy) was used, containing RT Buffer 10×, DNTP 25×, Random Primers 10×, Multi Scribe and DEPC water.

Extracted and quantified RNA was diluted to a concentration of 2 µg/mL and reverse transcribed into cDNA. A Master Mix of 10 µL (containing RT Buffer 10×, DNTP 25×, Random Primers 10×, Multi Scribe and water DEPC) was prepared, to which 10 µL of RNA (2 µg/mL) were added.

The samples were placed in a thermal cycler (Stratagene Mx3000P Real Time PCR System, Agilent Technologies Italy S.p.A., Milan, Italy) and subjected to retrotranscription under the following conditions:
25° C. for 10 minutes;
37° C. for 120 minutes;
85° C. for 1 minute;
25° C. for 2 minutes.

At the end of the retrotranscription, samples were added with 30 µL of DEPC water to obtain a final concentration of cDNA of 40 ng/µL.

qRT-PCR

The qRT-PCR is a real-time amplification and quantification method of amplified products by monitoring the fluorescence emitted during the reaction.

For RT-PCR amplification, the TaqMan® probe (Applied Biosystems) method was used. The following TaqMan probes were used: Hs00174128_m1 (TNF-α) and Hs999999_m1 (GAPDH). GAPDH (glyceraldehyde-3-phosphate dehydrogenase) was used as control gene (housekeeping).

The Taqman probe is a type of probe that allows the development of fluorescence as the amplification advances. A reporter (fluorophore FAM™) is bound to its 5' end while a quencher is bound to the 3' end. The closeness between the reporter and the quencher cancels the fluorescence signal emission. Only with the 5' esonucleasic activity 5' of thermostable DNA polymerase (Taq polymerase) fluorescence is detected and the accumulation of the amplification products can be evaluated through the increase of fluorescence of the reporter which increases with each cycle.

A Master Mix was set up for the qRT-PCR as follows:
10 µL di "2× TaqMan Universal PCR Master Mix" (containing AmpliTaq Gold DNA Polymerase, UNG-Amperasi®, dNTPs with dUTP, passive reference Rox II, optimized Buffer);
1 µL of "20× TaqMan Gene ExpressionAssays" (containing 2 primers and the fluorophore-labeled fluorescent probe FAM™);
5 µL of DEPC water.
4 µL of cDNA were added to the Master Mix for the target gene and 1 µL of cDNA for the housekeeping gene.

The amplification was carried out under the following conditions:
50° C. for 2 minutes (UNG-Amperasi® activation);
95° C. for 10 minutes (TaqMan polymerase activation);

95° C. for 15 seconds (denaturation);
60° C. for 1 minute (pairing-extension);
} 40 cycles Each analysis was conducted in triplicate.

The data obtained were analyzed according to the method of 2-ΔΔCt [133] and so it was possible to calculate the relative values of expression of the gene of interest, normalized compared to the housekeeping gene and calibrated on the control sample (untreated cells):

$$\Delta\Delta Ct = \Delta Ct_{target\text{-}housekeeping}(\text{control}) - \Delta Ct_{target\text{-}housing} (\text{treated cells})$$

The 2-ΔΔCt was calculated assuming an amplification efficiency of 100%.

Figure 3:
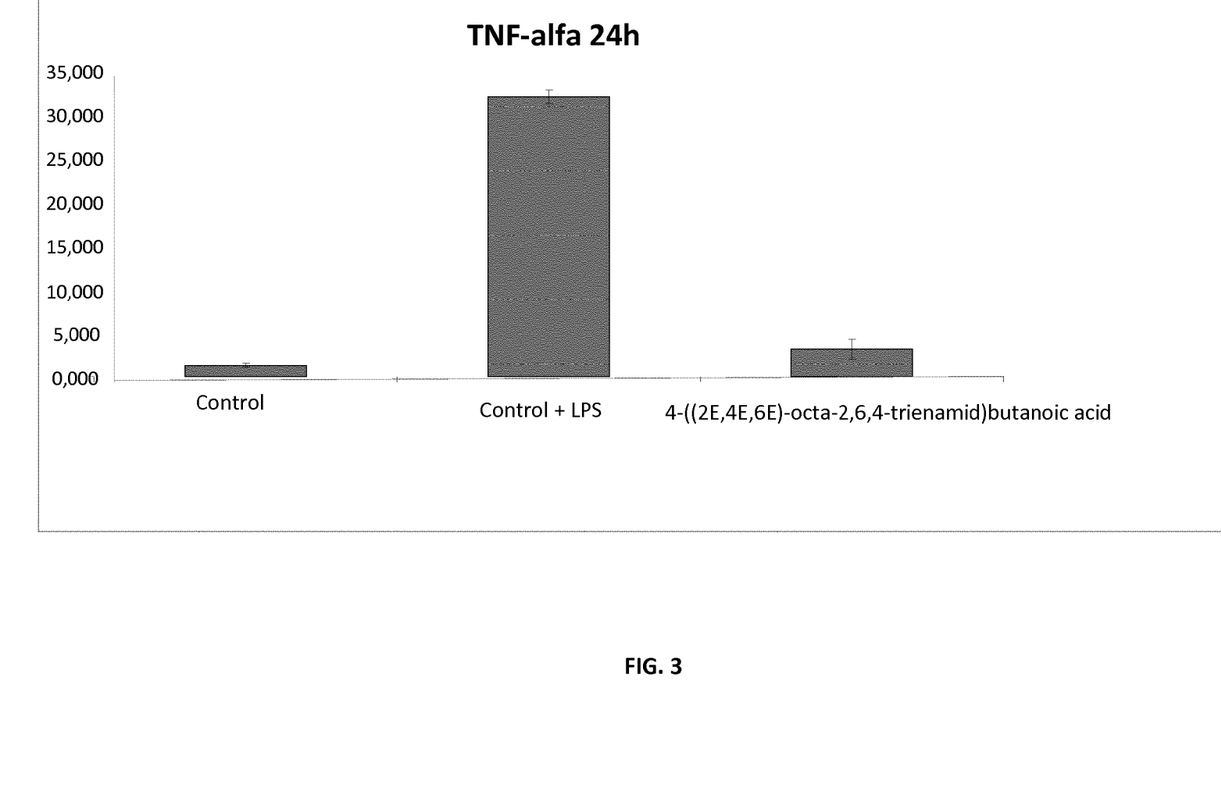
FIG. 3 shows a chart of the gene expression of TNF-alpha.

The results are summarized in the graph in FIG. 3, which shows a reduced expression of TNF-α for the compound of the invention compared to the positive control, and thereby an anti-inflammatory activity.

Study of the Effects on the Gene Expression of HAS1 (Hyaluronan Synthase 1) on Fibroblasts HAS1 is the gene for the synthesis of hyaluronic acid, one of the fundamental components of connective tissues able to impart resistance properties and retention of hydration, turgidity, plasticity and viscosity to the skin.

In this third test, the mouse fibroblast cell line Balb 3T3 Clone A31 (ATCC CCL-163™) (Aaronson and Todaro, 1968) was used, cultured in sterile flasks (25 cm$^3$), incubated at 37° C. in a humid atmosphere at 5% $CO_2$ in DMEM (Dulbecco's Modified Eagle's Medium) added with 10% bovine fetal serum (CBS), 1% non-essential amino acids, in the presence of 1% penicillin and streptomycin.

The 1:3 split is done every 2 days upon achieving the monolayer by washing with 1×PBS (phosphate buffer without $Ca^{2+}$ and $Mg^{2+}$) and detachment of cells with a trypsin-EDTA solution at 37° C. for 2 minutes.

When the cells reached a confluence of about 80%, they were detached with trypsin/EDTA and plated at a density of 1×10$^6$ cells per well in 12-well plates to perform the gene expression assay of HAS1.

Also in this case, a sample of GABA, γ-aminobutyric acid, was used as comparison compound at a concentration 0.5 µM.

The compound of the invention and GABA were dissolved in DMSO (100%) at a concentration of 10 mM (stock solution), and then diluted in DMEM, supplemented with 10% CBS, 1% NEAA solution and 1% penicillin (10,000 U/ml)/streptomycin (10,000 pg/ml).

A positive control, containing only culture medium, was included in each plate.

The cells were treated for 24 h with samples of the compound of the invention and GABA at a concentration equal to 2.5 and 5 µM. Each compound was assayed in replicate.

Gene expression of HAS1 in BALB3T3 cells was evaluated by relative quantitative RT-PCR (quantitative reverse transcription-polymerase chain reaction-qRT-PCR). This analysis required 3 sequential steps:
extraction of total RNA;
retrotranscription in cDNA;
qRT-PCR.

Total RNA was extracted from BALB3T3 cells using the commercial kit Ribospin™ (GeneAll Biotechnology Co., LTD).

At the end of incubation with the active compounds of interest, cells were washed with PBS (1×) and finally subjected to RNA extraction procedure. At the end of the extraction, using a spectrophotometer (Jenway UV/VIS MOD: 6715, BS-6715B0), concentrations were calculated in µg/mL of total RNA extracted at a wavelength of 260 nm.

Finally, the integrity of RNA (2 µg/mL) was assessed by means of an electrophoresis run on 1% agarose gel.

Total RNA was converted into cDNA (complementary DNA), using an enzyme capable of synthesizing a DNA molecule using a strand of RNA as a template; this DNA-polymerase RNA-dependent enzyme is called reverse transcriptase.

It binds to the 3' end of a single strand of RNA and using random primers and deoxynucleoside triphosphate (DNTPS) synthezises the strand of cDNA.

To this end, a commercial kit "High-Capacity cDNA Reverse Transcription Kit (Applied Biosystems, Monza, Italy) was used, containing RT Buffer 10×, DNTP 25×, Random Primers 10×, Multi Scribe and DEPC water.

Extracted and quantified RNA was diluted to a concentration of 2 µg/mL and reverse transcribed into cDNA. A Master Mix of 10 µL (containing RT Buffer 10×, DNTP 25×, Random Primers 10×, Multi Scribe and water DEPC) was prepared, to which 10 µL of RNA (2 µg/mL) were added.

The samples were placed in a thermal cycler (Stratagene Mx3000P Real Time PCR System, Agilent Technologies Italy S.p.A., Milan, Italy) and subjected to retrotranscription under the following conditions:

25° C. for 10 minutes;
37° C. for 120 minutes;
85° C. for 1 minute;
25° C. for 2 minutes.

At the end of the retrotranscription, samples were added with 30 µL of DEPC water to obtain a final concentration of cDNA of 40 ng/µL.

The qRT-PCR is a real-time amplification and quantification method of amplified products by monitoring the fluorescence emitted during the reaction.

For RT-PCR amplification, the TaqMan® probe (Applied Biosystems) method was used. The following TaqMan probes were used: Mm03048195_m1 (HAS1) and Mm00466519ml (β-actin). β-actin was used as control gene (housekeeping).

The Taqman probe is a type of probe that allows the development of fluorescence as the amplification advances. A reporter (fluorophore FAM™) is bound to its 5' end while a quencher is bound to the 3' end. The closeness between the reporter and the quencher cancels the fluorescence signal emission. Only with the 5' esonucleasic activity 5' of thermostable DNA polymerase (Taq polymerase) fluorescence is detected and the accumulation of the amplification products can be evaluated through the increase of fluorescence of the reporter which increases with each cycle.

A Master Mix was set up for the qRT-PCR as follows:
10 µL of "2× Premix Ex Taq";
1 µL of "20× TaqMan Gene Expression Assays" (containing 2 primers and the fluorophore-labeled fluorescent probe FAM™);
0.4 µL of passive reference Rox II;
5 µL of DEPC water.
4 µL of cDNA were added to the Master Mix for the target gene and 1 µL of cDNA for the housekeeping gene.

The amplification was carried out for 40 runs under the following conditions:
95° C., 30 sec (Amplitaq activation);
95° C., 5 sec (Denaturation)
60° C., 20 sec (Annealing—extension);
Each analysis was conducted in duplicate.

The data obtained were analyzed according to the method of $2^{-\Delta\Delta Ct}$ and so it was possible to calculate the relative values of expression of the gene of interest, normalized compared to the housekeeping gene and calibrated on the control sample (untreated cells):

$$\Delta\Delta Ct = \Delta Ct_{target-housekeeping}(\text{control}) - \Delta Ct_{target-housekeeping}(\text{treated cells})$$

The $2^{-\Delta\Delta Ct}$ was calculated assuming an amplification efficiency of 100%.

Figure 4:
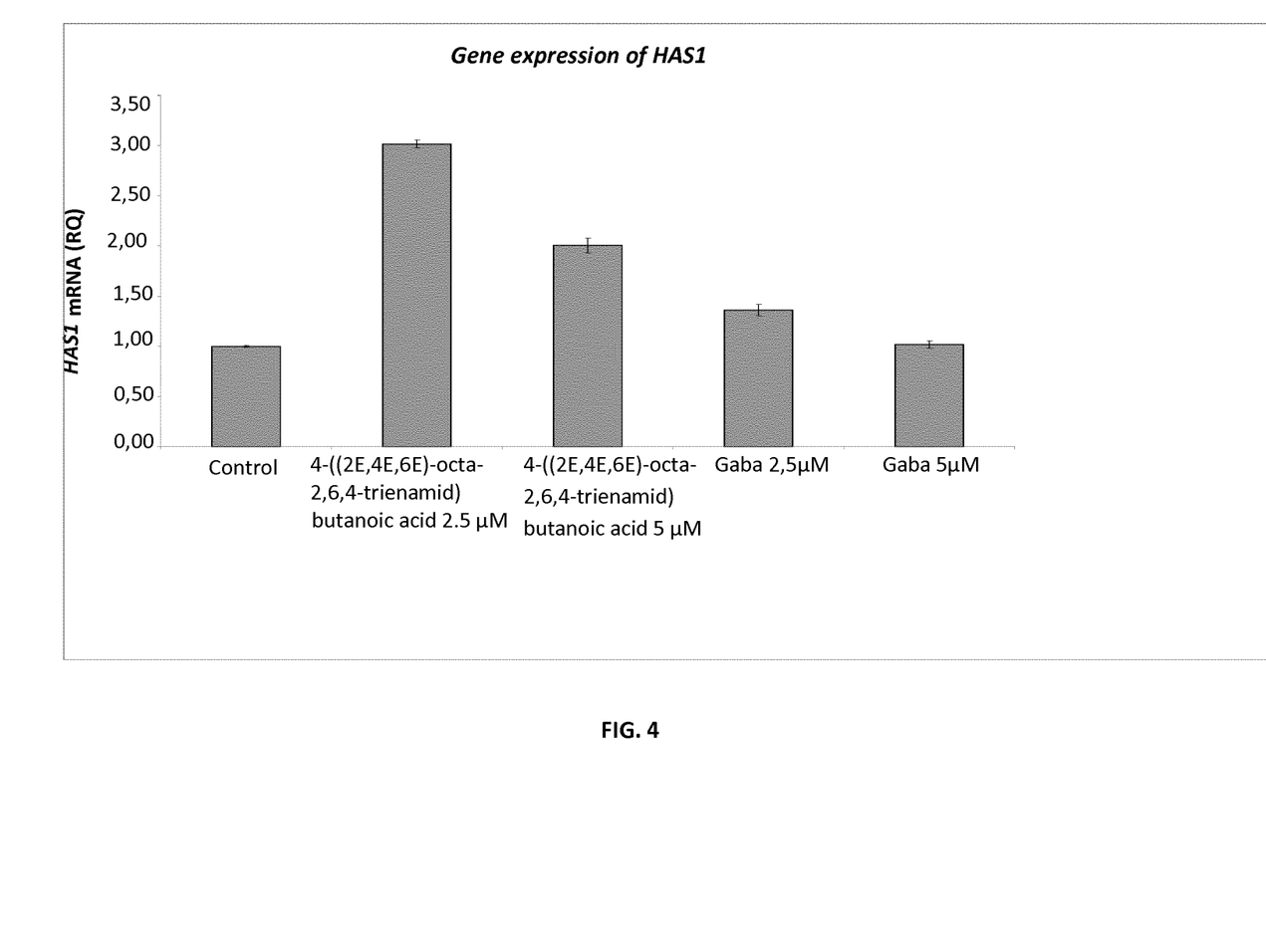
FIG. 4 shows a chart of the gene expression of HAS1.
Figure 5:
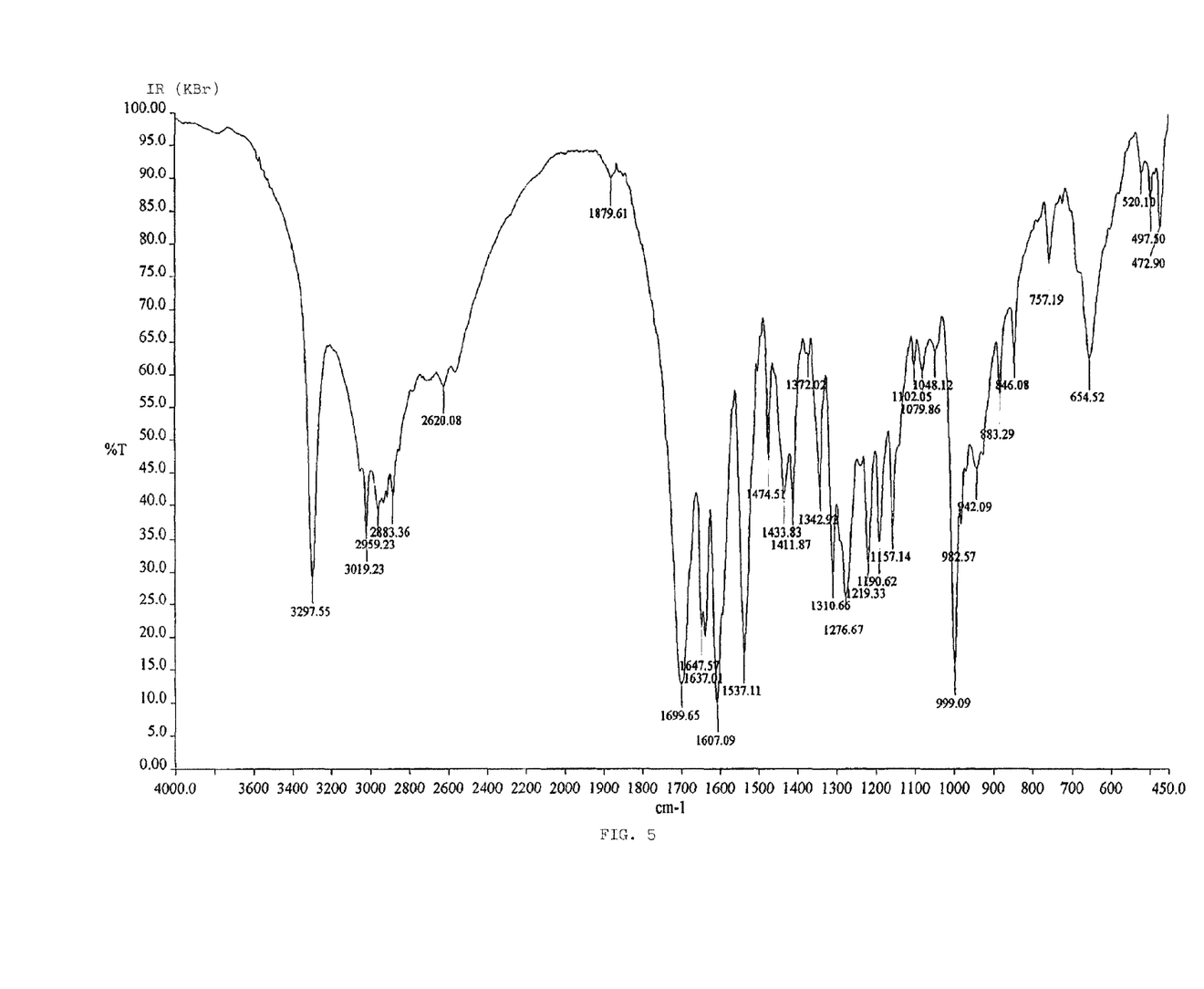
FIG. 5 shows the IR spectrum (KBr) of 4-((2E,4E,6E)-octa-2,6,4-trienamid)butanoic acid.
Figure 6:
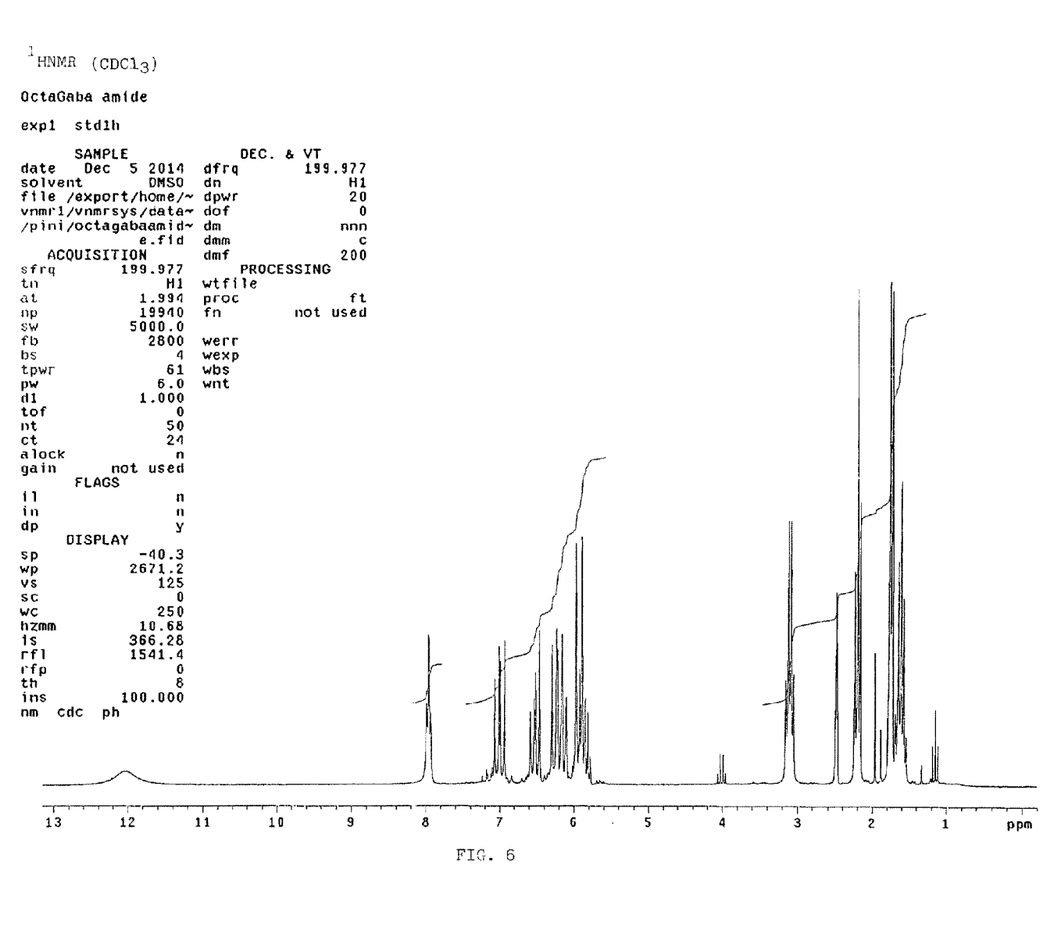
FIG. 6 shows the spectrum $^1$H NMR (CDCl$_3$) thereof.
Figure 7:
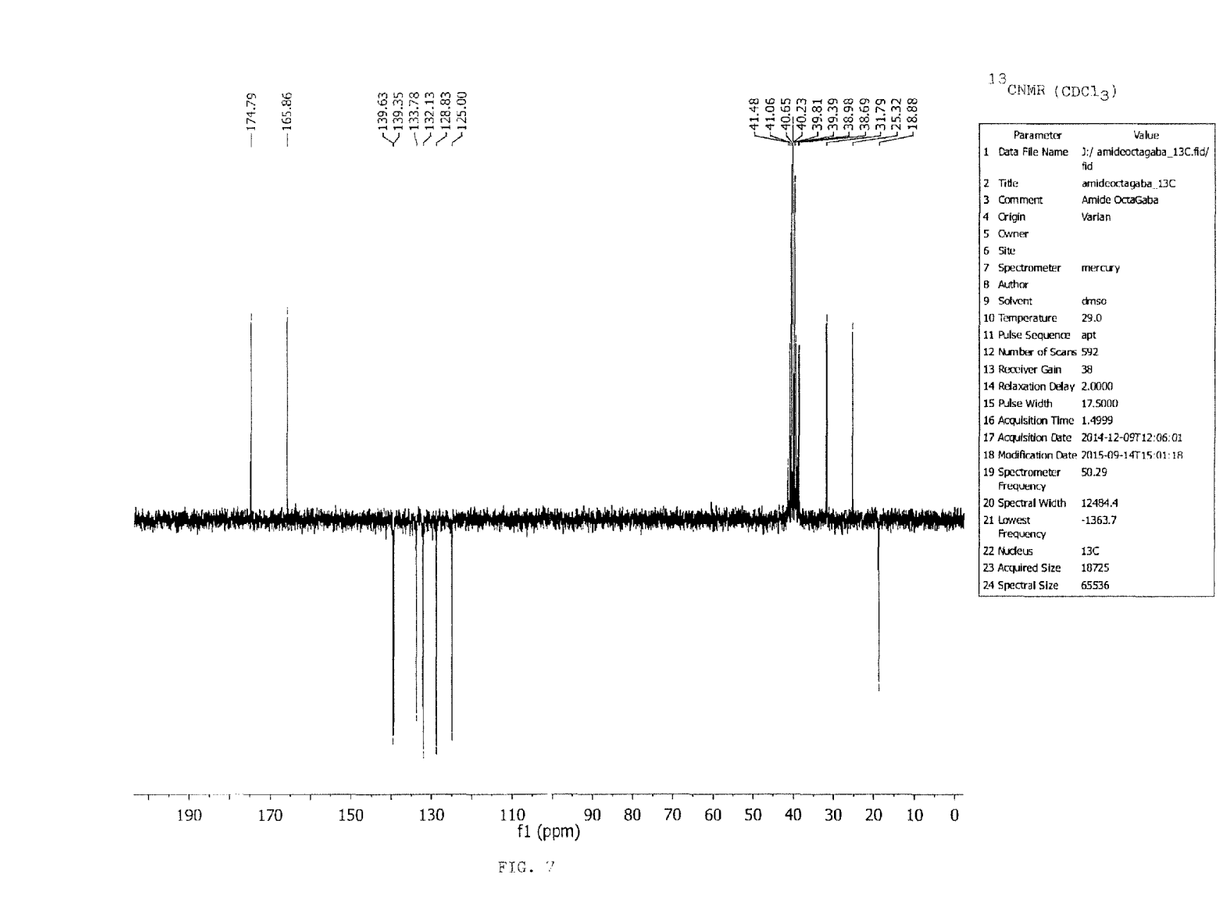
FIG. 7 shows the spectrum $^{13}$C NMR (CDCl$_3$) thereof.
Figure 8:
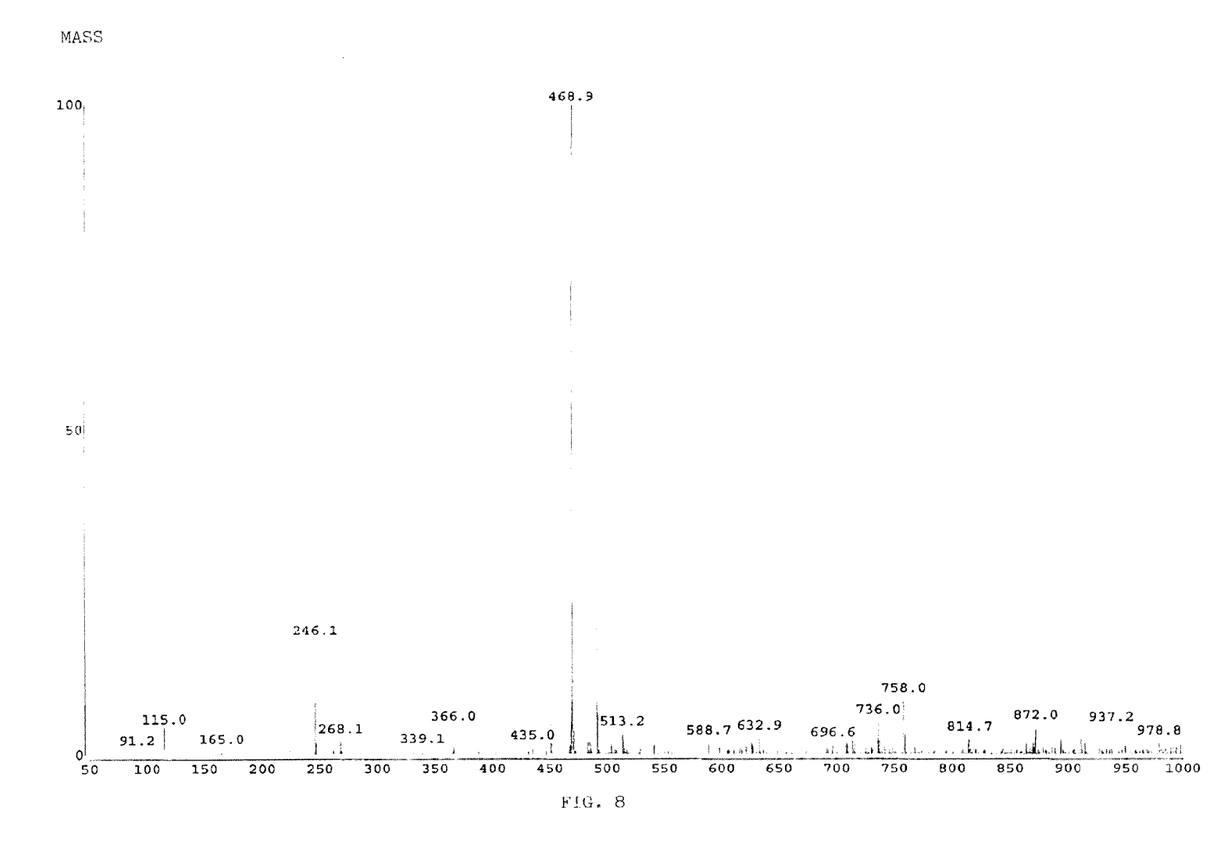
FIG. 8 shows the mass spectrum.

The results are summarized in the graph in FIG. 4, which highlights an increased gene expression of HAS1 for the compound of the invention, higher than the reference compound at both concentrations tested. Since HAS1 is the gene for the synthesis of hyaluronic acid, the usefulness of the compound of the invention in imparting resistance properties and retention of hydration, turgidity, plasticity and viscosity typical of hyaluronic acid is understood.

The invention claimed is:

1. A compound 4-((2E, 4E, 6E)-octa-2,4,6-trienamid) butanoic acid of formula:

2. A composition comprising 4-((2E, 4E, 6E)-octa-2,4,6-trienamid) butanoic acid or a pharmaceutically acceptable salt thereof, as the active ingredient, and excipients for topical administration on the skin.

3. The composition according to claim 2, wherein the amount of 4 ((2E, 4E, 6E)-octa-2,4,6-trienamid) butanoic acid, or pharmaceutically acceptable salt thereof, in the composition is in the range from 0.4 mM to 56 mM.

4. The composition according to claim 2, wherein the amount of 4 ((2E, 4E, 6E)-octa-2,4,6-trienamid) butanoic acid, or pharmaceutically acceptable salt thereof, in the composition is expressed as parts by weight, w/w (%) in one of the following ranges: 0.01-0.05; 0.125-0.375; 0.25-0.75; 0.5-1; 0.75-1.25.

5. A method for treating a dermatological inflammatory disease in a human subject comprising:
administering topically to the human subject's skin afflicted with the inflammatory disease, the compound of claim 1 or a pharmaceutically acceptable salt thereof.

6. The method of claim 5, wherein the dermatological inflammatory disease is a skin sensitization condition, allergic contact dermatitis, or skin rash.

7. A method for preserving the physiological conditions of the epidermis of a human subject and for maintaining skin homeostasis in the human subject, said method comprising:
administering topically to the skin of the human subject in need thereof, the compound of claim 1 or a pharmaceutically acceptable salt thereof.

8. A method for promoting production of hyaluronic acid in skin of a human subject, said method comprising:
administering topically to the skin of the human subject in need thereof, the compound of claim 1 or a pharmaceutically acceptable salt thereof.

9. A method for treating aging skin of a human subject, said method comprising:
administering topically to the aging skin of the human subject in need thereof, the compound of claim 1 or a pharmaceutically acceptable salt thereof.

10. A method for producing an antioxidant activity in skin of a human subject, said method comprising:
administering topically to the skin of the human subject in need thereof, the compound of claim 1 or a pharmaceutically acceptable salt thereof.

* * * * *

UNITED STATES PATENT AND TRADEMARK OFFICE
CERTIFICATE OF CORRECTION

PATENT NO. : 9,944,591 B2
APPLICATION NO. : 15/501997
DATED : April 17, 2018
INVENTOR(S) : Giuliani et al.

Page 1 of 1

It is certified that error appears in the above-identified patent and that said Letters Patent is hereby corrected as shown below:

In the Claims

In Claim 3, at Column 12, Line 27, please delete "4 ((2E, 4E, 6E)-octa-2,4,6-trienamid)" and insert -- 4-((2E, 4E, 6E)-octa-2,4,6-trienamid) --

In Claim 4, at Column 12, Line 31, please delete "4 ((2E, 4E, 6E)-octa-2,4,6-trienamid)" and insert -- 4-((2E, 4E, 6E)-octa-2,4,6-trienamid) --

Signed and Sealed this
Tenth Day of July, 2018

Andrei Iancu
*Director of the United States Patent and Trademark Office*